United States Patent
Harel et al.

(10) Patent No.: US 10,117,839 B2
(45) Date of Patent: Nov. 6, 2018

(54) ENCAPSULATION OF HYDROPHOBIC BIOLOGICALLY ACTIVE COMPOUNDS

(71) Applicant: Intervet Inc., Madison, NJ (US)

(72) Inventors: Mordechai Harel, Pikesville, MD (US); Majid Keshtmand, Baltimore, MD (US); Swetha Kambalapally, Ellicott City, MD (US); Sara Morrison-Rowe, Gaithersburg, MD (US)

(73) Assignee: Intervet Inc., Madison, NJ (US)

( * ) Notice: Subject to any disclaimer, the term of this patent is extended or adjusted under 35 U.S.C. 154(b) by 0 days.

(21) Appl. No.: 14/817,307

(22) Filed: Aug. 4, 2015

(65) Prior Publication Data

US 2016/0038428 A1 Feb. 11, 2016

Related U.S. Application Data (60) Provisional application No. 62/033,365, filed on Aug. 5, 2014.

(51) Int. Cl.

| | |
|---|---|
| A61K 9/50 | (2006.01) |
| A61K 9/16 | (2006.01) |
| A61K 9/51 | (2006.01) |
| A61K 31/07 | (2006.01) |
| A61K 35/60 | (2006.01) |
| A61K 31/00 | (2006.01) |
| A23K 40/30 | (2016.01) |
| A23K 20/158 | (2016.01) |
| A23P 10/30 | (2016.01) |
| A23L 29/212 | (2016.01) |
| A23L 29/219 | (2016.01) |
| A23L 29/25 | (2016.01) |
| A23L 29/281 | (2016.01) |
| A23L 33/115 | (2016.01) |

(52) U.S. Cl.
CPC .......... *A61K 9/5052* (2013.01); *A23K 20/158* (2016.05); *A23K 40/30* (2016.05); *A23L 29/212* (2016.08); *A23L 29/219* (2016.08); *A23L 29/25* (2016.08); *A23L 29/281* (2016.08); *A23L 29/284* (2016.08); *A23L 33/115* (2016.08); *A23P 10/30* (2016.08); *A61K 9/1652* (2013.01); *A61K 9/5073* (2013.01); *A61K 9/5169* (2013.01); *A61K 31/00* (2013.01); *A61K 31/07* (2013.01); *A61K 35/60* (2013.01); *A23V 2002/00* (2013.01)

(58) Field of Classification Search
CPC ... A23K 1/004; A23L 1/0047; A23V 2002/00; A61K 35/60; A61K 9/5052
See application file for complete search history.

(56) References Cited

U.S. PATENT DOCUMENTS

| | | | |
|---|---|---|---|
| 2,973,266 A | 2/1961 | Rosenberg | |
| 4,217,370 A | 8/1980 | Rawlings et al. | |
| 4,790,998 A | 12/1988 | Swartz | |
| 5,418,010 A | 5/1995 | Janda et al. | |
| 6,608,017 B1 * | 8/2003 | Dihora ................ A23L 1/22016 | |
| | | | 424/490 |
| 8,663,690 B2 | 3/2014 | Gheith et al. | |
| 2004/0017017 A1 | 1/2004 | Van Lengerich et al. | |
| 2007/0098853 A1 | 5/2007 | van Lengerich et al. | |
| 2007/0154619 A1 | 7/2007 | Bialex et al. | |
| 2010/0172831 A1 | 7/2010 | Mason et al. | |

FOREIGN PATENT DOCUMENTS

| | | |
|---|---|---|
| GB | 2004727 A | 4/1979 |
| WO | 2004009054 A2 | 1/2004 |
| WO | 2004041251 A1 | 5/2004 |
| WO | 2008085997 A2 | 7/2008 |
| WO | 2008143507 A2 | 11/2008 |
| WO | WO 2009/070011 A1 | 6/2009 |
| WO | WO 2009070011 A1 * 6/2009 ........... A23D 7/0053 |
| WO | 2010141821 A1 | 12/2010 |

OTHER PUBLICATIONS

International Search Report for International Application No. PCT/US2015/043564 dated Nov. 9, 2015.
Chen and Subirade, Biomaterials, 26(30):6041-53 (2005).
Chen et al., Trends Food Sci Technol, 17(5):272-83 (2006).
Hong and McClements, J Agric Food Chem, 55(14):5653-60 (2007).
Jafari et al., Food Research International, 41:172-73 (2007).
Jameson et al., Int Dairy J, 12(4):319-29 (2002).
Jones. and McClements, Food Biophysics, 3(2):191-97 (2008).
Kolanowski et al., J Amer Oil Chem Soc, 84:37-45 (2007).
Semo et al., Food Hydrocolloids, 21 (5-6):936-42 (2007).
Na et al., Biotechnology and Bioprocess Engineering, 16:1077-82 (2011).
Wang et al., J. Diary Sci., 80:1047-53 (1997).
Wang et al., J. Diary Sci., 80:1054-59 (1997).
Zimet and Livney, Food Hydrocolloids, 23(4):1120-26 (2009).
Bing Hua, Biopolymer Based Nano-Delivery Systems for Enhancing Bioavailability of Nutraceuticals, Chinese Journal of Polymer Science, 2013, p. 1190, vol. 31, No. 9.
Extended EP Search report for15830310.7 dated Nov. 29, 2017.
Qin et al., Water-solubility of Chitosan and its Antimicrobial Activity, Carbohydrate Polymers, 2006, 367-374, 63.

* cited by examiner

Primary Examiner — Michael B. Pallay (57) ABSTRACT

A composition comprising hydrophobic droplets coated by a shell and dispersed in a matrix and a consumable product comprising the composition are provided. The hydrophobic droplets comprise a hydrophobic compound, the shell comprises an irreversibly denatured protein, and the matrix comprises a protein, a starch, and a polysaccharide. Also provided are methods for preparing the composition and the consumable product.

18 Claims, 4 Drawing Sheets

FIG. 1

FIG. 2 a) After homogenizing
b) After acid treatment
c) After heat treatment

FIG. 3

I. Oil suspension after acid reaction

H. Coated oil suspension after both acid and heat reactions

ENCAPSULATION OF HYDROPHOBIC BIOLOGICALLY ACTIVE COMPOUNDS

CROSS-REFERENCE TO RELATED APPLICATION

This application is related to and claims the benefit of U.S. Provisional Application No. 62/033,365 filed on Aug. 5, 2014, the contents of which are incorporated herein by reference.

FIELD OF THE INVENTION

The present invention relates to protection of sensitive hydrophobic compounds in a dry polymeric matrix, more particularly sensitive hydrophobic compounds encapsulated in food, animal feed, nutraceutical products, and pharmaceutical products.

BACKGROUND OF THE INVENTION

Certain functional hydrophobic compounds have beneficial health effects. Hydrophobic compounds such as oil-soluble vitamins (e.g., vitamin A, D, E and K), carotenes, omega-3, and omega-6 essential fatty acids constitute important components of cell membranes, regulate many metabolic pathways, and control the production of substances that affect other biological processes. For example, eicosapentaenoic acid (EPA) and docosahexaenoic acid (DHA), long-chain forms of omega-3 fatty acids, are known to support brain and cardiovascular health. However, many hydrophobic compounds are sensitive to oxidation when exposed to air, humidity and/or light, and degrade rapidly in consumable products, often resulting in the release of unpleasant fishy odors and tastes.

It would be desirable to protect sensitive hydrophobic compounds in consumable products from oxidation and to eliminate an unpleasant taste or after-taste and odor at the time of consumption. It would also be desirable to stabilize sensitive hydrophobic compounds in the form of dry and flowable powder suitable for use in dry consumable products such as dry food, animal feed, supplements and pharmaceutical products.

SUMMARY OF THE INVENTION

The present invention provides a composition comprising hydrophobic droplets coated by a shell and dispersed in a matrix. The hydrophobic droplets comprise a hydrophobic compound. The shell comprises an irreversibly denatured protein. The matrix comprises a protein, a starch, and a polysaccharide. The composition comprises less than 20 wt % water.

The hydrophobic compound may be a biologically active or bioactive agent selected from the group consisting of vitamins, antibiotics, carotenoids, plant extracts, fruit extracts, vegetable extracts, antioxidants, lipids, steroids, phytochemicals and drugs.

The irreversibly denatured protein may be prepared by applying two different external stressors, wherein each external stressor is selected from the group consisting of an acid, a base, an inorganic salt, an enzyme, an organic solvent, heat and sheer force.

The droplets may have a particle size within the range of 0.1 µm to 5.0 µm. The hydrophobic droplets may further comprise an edible oil selected from the group consisting of vegetable oils, animal oils, marine oils, and microalgae oils. The vegetable oil may be selected from the group consisting of rice bran oil, flaxseed oil, and oil comprising an omega-3 fatty acid or a conjugated linoleic acid. The animal oil may be selected from the group consisting of marine oil, fish oil, and egg oil. The microalgae oil may comprise an omega-3 fatty acid, an omega-6 fatty acid, or a conjugated linoleic acid.

The ratio between the irreversibly denatured protein and the hydrophobic compound may be within the range of 0.1:1 to 1:1 by weight.

The protein in the matrix may be a globular or randomly coiled protein, which may be selected from the group consisting of dairy proteins, gelatin, corn zein proteins, bovine serum albumin, egg albumin, proteins from wheat, barley, rye or oats, vegetable proteins, microbial proteins, legume proteins, proteins from tree nuts, and proteins from ground nuts.

The polysaccharide may be selected from the group consisting of pectin, alginic acid and salts thereof, xanthan gum, chitosan, dextran, pullulan, chondroitin sulfate, gum arabic, gum karaya, gum tragacanth, and carrageenan.

The starch may be hydrophobically modified.

The matrix may further comprise a polymer selected from the group consisting of ethyl cellulose, HPMC Eudragit E, Eudragit E 100, and Eudragit E PO.

The composition may further comprise an antioxidant selected from the group consisting of phospholipids, alpha-lipoic acid, citric acid, Vitamin C and esters thereof, green tea polyphenols, green tea extracts, grape seed extracts, resveratrol, quercetin, cinamic acid and salts thereof, ferulic acid and salts thereof, rosemarinic acid and salts thereof, carotenoids (e.g., $\alpha$-, $\beta$-, and $\gamma$-carotene, lutein, astaxanthin, zeaxanthin), curcuminoids, superoxide dismutase, glutathione peroxidase, tocoferoles, tocotrienols, polyphenols, Coenzyme Q10, cysteine, methionine, and a combination thereof.

The present invention also provides a method of preparing a composition. The method comprises (a) reducing the pH of a suspension comprising a hydrophobic compound and a protein to below the isoelectric point (pKa) of the protein; (b) irreversibly denaturing the protein in the suspension of step (a), whereby hydrophobic droplets coated by a shell comprising the irreversibly denatured protein are formed, wherein the hydrophobic droplets comprise the hydrophobic compound; (c) mixing the coated hydrophobic droplets of step (b) with a protein, a starch, and a polysaccharide to form a mixture; and (d) drying the mixture of step (c), whereby a composition comprising the coated hydrophobic droplets dispersed in a matrix is prepared, wherein the matrix comprises the protein, the starch, and the polysaccharide, and wherein the composition comprises less than 20 wt % water.

The irreversibly denatured protein may be selected from group consisting of milk proteins and egg proteins, and the shell of step (b) may comprise at least 60 wt % of the irreversible denatured protein.

The composition prepared according to the preparation method of the present invention is also provided.

A consumable product comprising the composition of the present invention is further provided. The consumable product has a therapeutic, nutritional, or disease-preventive effect. The product may be selected from the group consisting of food products, nutritional products, ready-to-drink mixes, supplements in the form of powder, tablet or capsule, vitamin premixes, pelleted animal feed or supplements or premixes, nutraceutical products, pharmaceutical products, and drugs.

BRIEF DESCRIPTION OF THE DRAWINGS

FIG. 1 is a schematic drawing illustrating the production of a dry fish oil composition according to some embodiments. The fish oil particulate material may be made by multiple methods. Fish oil is admixed with a non-denatured protein, and the mixture is homogenized, sonicated or, alternatively, microfluidized. The pH of the homogenized mixture is reduced to just below the iso-electric point of the non-denatured protein and then exposed to a physical, chemical or enzymatical reaction such that a coat/shell of the irreversible denatured protein is formed around the fish oil droplets. The homogenized mixture is passed through a heat exchanger and briefly exposed to a temperature sufficient to irreversibly denature the protein and forming coated fish oil droplets. The coated fish oil droplets are then admixed with a mixture of water soluble polymers forming a wet fish oil composition. The wet fish oil composition is then extruded or atomized, and dried, grounded, and sized to yield a dry fish oil composition.

DETAILED DESCRIPTION OF THE INVENTION

The present invention relates to compositions comprising stable hydrophobic compounds and methods for preparation and use thereof. Such compositions may be incorporated into food animal feed, nutraceutical and pharmaceutical products such as nutritional bars, breakfast cereals, bakery products, drink mixes, supplements, tablets and pelleted feed. Encapsulation of hydrophobic compounds in polymeric matrices according to the present invention reduces undesirable effects (e.g., oxidation, off flavor, and unpleasant aroma) and improves shelf life and bioavailability as well overall physiological efficacy of consumable products comprising the hydrophobic compounds.

The present invention is based on the discovery of the formation of a stable coat or shell surrounding microscopic oil droplets by irreversible denatured proteins, which coated oil droplets retain dispersability and small particle size, and show emulsion stability even without addition of an emulsifier or surfactant. Moreover, over 90% of the oil may be protected by shell forming proteins and substantially free of surface oil, which is uncoated oil or oil sticking to the outside of the coat or shell. Such encapsulation provides better protection of hydrophobic compounds against degradation and oxidation when further embedded in a polymeric matrix.

According to one aspect of the invention, a composition is provided. The composition comprises hydrophobic droplets. The hydrophobic droplets are coated by a shell. The coated hydrophobic droplets are dispersed in a matrix. The hydrophobic droplets comprise a hydrophobic compound. The shell comprises one or more irreversibly denatured proteins. The matrix comprises one or more matrix polymers selected from the group consisting of proteins, starches, and polysaccharides. The composition may be dry. The water content of the composition is less than about 50, 40, 30, 20, 10, 5, or 1 wt %, preferably less than about 20 wt %.

Alternatively, the composition comprises a hydrophobic compound. In this composition, more than about 1, 5, 10, 20, 30, 40, 50, 60, 70, 80, 90, 95 or 99 wt %, preferably at more than about 5 wt %, of the hydrophobic compound is in hydrophobic droplets. The hydrophobic droplets are coated by a shell, and dispersed in a matrix. The shell comprises one or more irreversibly denatured proteins. The matrix comprises one or more matrix polymers selected from the group consisting of proteins, starches, and polysaccharides. The composition may be dry. The water content of the composition is less than about 50, 40, 30, 20, 10, 5, or 1 wt %, preferably less than about 20 wt %.

The terms "hydrophobic" and "lipophilic" are used herein interchangeably, and refer to a material whose solubility is greater in non-polar solvent having a dielectric constant of less than about 15, for example, long chain alcohols, than in an aqueous solution.

The hydrophobic compound may have a therapeutic, nutritional, or disease-preventive effect. It may be natural or synthetic. Preferably, the hydrophobic compound is insoluble in an aqueous solution. The hydrophobic compound may be a bioactive agent selected from the group consisting of vitamins, antibiotics, carotenoids, plant extracts, fruit extracts, vegetable extracts, antioxidants, lipids, steroids, phytochemicals, essential fatty acids, nutraceuticals, pharmaceuticals, and drugs.

Exemplary vitamins include vitamin A, vitamin D, vitamin E and vitamin K, and salts or derivatives thereof. The vitamin may be derived from any source. Vitamin D may be selected from the group consisting of vitamin D2 (ergocalciferol), vitamin D3 (cholecalciferol), other vitamin D, and salts or derivatives thereof. Vitamin E may be selected from the group consisting of $\alpha$, $\beta$, $\gamma$, or $\delta$-tocopherols, $\alpha$, $\beta$, $\gamma$, or $\delta$-tocotrienol, other vitamin E, and salts (e.g., vitamin E phosphate) or derivatives (e.g., tocopheryl sorbate, tocopheryl acetate, tocopheryl succinate, and other tocopheryl esters) thereof. Vitamin A may be selected from the group consisting of retinol, retinal, retinoic acid, other vitamin A, or salts or derivatives thereof (e.g., Vitamin A acetate, and Vitamin A palmitate). Vitamin K may be selected from the group consisting of vitamin K1 (phytonadione), vitamin K2 (menaquinone), vitamin K3 (menadione), vitamin K4, vitamin K5, vitamin K6, vitamin K7, and salts or derivatives thereof.

The term "antioxidant" used herein refers to an agent capable of slowing or preventing oxidation of other agents or molecules. The examples of antioxidants include phospholipids (e.g., soy or egg lecithin, phosphatidyl-choline, phosphatidyl ethanolamine, phosphatidyl-serine), a racemic mixture of $\alpha$-lipoic acid, Vitamin C and esters thereof, green tea polyphenols, green tea extracts, grape seed extracts, resveratrol, cinamic acid and salts thereof, ferulic acid and salts thereof, rosemarinic acid and salts thereof, carotenoids (e.g., $\alpha$-, $\beta$-, and $\gamma$-carotene, lutein, astaxanthin, and zeaxanthin), curcuminoids such as curcumin, chlorophyllin and salts thereof, superoxide dismutase, glutathione peroxidase, tocotrienols, polyphenols, cysteine, methionine and mixtures thereof.

An essential fatty acid may be saturated, polyunsaturated, or monounsaturated, and may be found in nature or produced synthetically. Exemplary essential fatty acids include sterols such as cholesterol and derivatives thereof, prostaglandins, lecithin, choline, inositol, conjugated linolenic acid, myristic acid, palmitic acid, stearic acid, omega-3 fatty acids (e.g., docosahexaenoic acid (DHA), eicosapentaenoic acid, α-linolenic acid, stearidonic acid eicosatrienoic acid, eicosatetraenoic acid, docosapentaenoic acid and glycerol ester derivatives thereof), omega-6 fatty acids (e.g., linoleic acid, gamma-linolenic acid, eicosadienoic acid, dihomo-gamma-linolenic acid, arachidonic acid, docosadienoic acid, adrenic acid, docosapentaenoic acid and calendic acid), omega-9 fatty acids (e.g., oleic acid, eicosenoic acid, mead acid, erucic acid and nervonic acid), precursors of fatty acids, and derivatives of fatty acids.

A nutraceutical, also known as functional food, may be food or a part of food that promotes health, prevents a disease, or enhances well-being. Examples of nutraceuticals include antioxidants, phytochemicals, phytoestrogens, carotenes, pantothenate, folic acid, pro-vitamins, Coenzyme Q10, fish oil, essential and/or highly unsaturated fatty acids, and mid-chain triglycerides and mixtures thereof. "Phytoestrogens" or "dietary estrogens" as used herein refers to naturally occurring non-steroidal plant compounds possessing estrogenic activity. Examples of phytosterols include isoflavones genistin, genistein, daidzein, daidzin, malonyl daidzin, glycitin, malonyl glycitin, acetyl glycitin, acetyl daidzin, acetyl genistin, glycitein, and mixtures thereof), stilbenoids trans-resveratrol), lignans (e.g., pinoresinol, podophyllotoxin, steganacin, matairesinol, lariciresinol, secoisolariciresinol, hydroxymatairesinol, syringaresinol and sesamin) and coumestans (e.g., coumestrol, wedelolactone, plicadin), beta-sitosterol, campesterol, ergosterol (e.g., provitamin D2), brassicasterol, delta-7-stigmasterol and delta-7-avenasterol. Other nutraceticals may include fruit extracts, vegetable extracts, phospholipids (e.g. phosphatidyl-serine), proteoglycans (e.g., decorin, biglycan, fibromodulin and lumican), certain amino acids (e.g., iso-leucine, leucine, methionine, phenylanine, tryptophan, and valine), food additives, phytonutrients (e.g., lutein, zeaxanthin and astaxanthin), plant oils, fish and marine animal oils and algae oils.

A pharmaceutical may be a medicinal drug. According to some preferred embodiments, the pharmaceutical of the present invention is hydrophobic. Such pharmaceuticals may optionally comprise any type of material that is hydrophobic, insoluble in an aqueous solution and/or at physiological pH, and/or pH sensitive, which material may be selected from the group consisting of plant alkaloids and the like, drugs with multi-cyclic ring structures (e.g., those that lack polar groups), peptides and proteins (e.g., antibodies, vaccines and enzymes), oligonucleotides, polynucleotides (e.g., siRNA molecules and the like), and other biopolymers.

The droplets may further comprise an edible oil. The edible oil may be selected from the group consisting of vegetable oils, animal oils, marine oils, and microalgae oils. The vegetable oil may be selected from the group consisting of rice bran oil, flaxseed oil, and oil comprising one or more omega-3 fatty acids or a conjugated linoleic acid. The animal oil may be selected from the group consisting of marine oil, fish oil and egg oil. The microalgae oil may comprise one or more omega-3 fatty acids, one or more omega-6 fatty acids, or a conjugated linoleic acid. The edible oil may be rich (e.g., comprising at least about 5, 10, 20, 30, 40, 50, 60, 70, 80, 90 or 95 wt %) in the omega-3 fatty acids or the conjugated linoleic acid.

In certain embodiments, the hydrophobic compounds include fat soluble vitamins, (e.g., vitamins A, D, E, and K), tocotrienols, carotenoids, xanthophylls (e.g., lycopene, lutein, astaxanthin, and zeazanthin), fat-soluble nutraceuticals including phytosterols, stanols and esters thereof, Coenzyme Q10 and ubiquinol, hydrophobic amino acids and peptides, essential oils and extracts, and fatty acids. Fatty acids may include conjugated linolenic acid (CLA), omega-6 fatty acids, and omega-3 fatty acids. Suitable omega-3 fatty acids include short-chain omega-3 fatty acids such as alpha-linolenic acid (ALA), which are derived from plant sources, for example, flaxseed, and long-chain omega-3 fatty acids such as eicosapentaenoic acid (EPA) and docosahexaenoic acid (DHA). The long-chain omega-3 fatty acids can be derived from, for example, marine fish oils. Such oils can be extracted from various types of fish or marine animals, such as anchovies, capelin, cod, herring, mackerel, menhaden, salmon, sardines, shark and tuna, or from microorganisms such as micro-algae, or a combination thereof.

The term "irreversibly denatured protein" as used herein refers to a protein that has lost irreversibly its native tertiary structure and secondary structure upon exposure to one or more external stressors. An irreversibly denatured protein is not capable of regaining its native after the removal of the external stressor(s). The native structure is the tertiary or secondary structure of a protein when produced naturally or synthetically.

The irreversible denatured protein may be selected from milk proteins and egg proteins. Milk proteins and egg proteins offer the potential for encapsulation of hydrophobic compounds. (Chen et al., (2006) Trends in Food Sci. and Technology 17, 272; Semo et al., (2007) Food Hydrocolloids 21,936), Milk and egg proteins have naturally evolved to deliver stable emulsions of oil rich nutrients from mother to neonate. In particular, egg albumen and β-lactoglobulin are suitable vehicles for delivery of hydrophobic biologically active compounds, as they bind a variety of lipophilic micronutrients. (Wang et al., (1997a) J. Dairy Sci. 80:1047; Wang et al., (1997b) J. Dairy Sci. 80:1054; Zimet and Livney (2009) Food Hydrocolloids 23:1120). In one embodiment, the proteins are dissolved in a solution in their native form while their tertiary structures and secondary structures remain intact before a hydrophobic compound is added to form a uniform suspension.

The ratio between the irreversibly denatured protein and the hydrophobic compound may be within the range from about 0.1:1 to about 1:1 by weight, preferably from about 0.2:1 to about 0.8:1 by weight, more preferably from about 0.3:1 to about 0.6:1 by weight.

The coated hydrophobic droplets may have a particle size within the range of about 0.1 µm to about 5.0 µm. More than about 50% of the coated droplets may have a particle size within the range of about 0.1 µm to about 1.0 µm, preferably within the range of about 0.3 µm to about 0.7 µm.

The composition of the present invention may comprise one or more matrix polymers selected from the group consisting of proteins, starches, and polysaccharides. The protein may be a globular or randomly coiled protein. Exemplary globular or randomly coiled proteins include dairy proteins (e.g., whey proteins, caseins and fractions thereof), gelatin, corn zein proteins, bovine serum albumin, egg albumin, grain protein extracts (e.g., proteins from wheat, barley, rye or oats), vegetable proteins, microbial proteins, legume proteins, proteins from tree nuts, proteins from ground nuts, or combinations thereof.

The composition of the present invention may comprise one or more starch. The starch may be a natural starch or a derivative thereof. A starch derivative is preferably a hydrophobically modified starch, which may be produced in the industry by replacing the hydroxyl groups in the starch backbone polymer with ester, methyl, ether or other hydrophobic groups such as fatty acids. A modified food starch derived from waxy maize (HI-CAP® 100 manufactured by Ingredion, Westchester, Ill.) is an especially preferred matrix polymer due to its excellent oil absorbance capacity and resistance to oxidation.

The composition of the present invention may comprise one or more polysaccharides. The polysaccharide may be selected from the group consisting of pectin, alginic acid and salts thereof, xanthan gum, chitosan and derivatives thereof, dextran, pullulan, chondroitin sulfate, gum arabic, gum karaya, gum tragacanth, carrageenan, and combinations thereof.

The matrix may further comprise a polymer or a combination of polymers. The polymer may provide controlled release or gastric resistancy of the hydrophobic compound. Non limiting examples of the polymers include ethyl cellulose, HPMC Eudragit E, Eudragit E 100, and Eudragit E PO.

Many possible combinations of polymers are useful for forming the matrix. Exemplary polymer mixtures for use in the dry composition disclosed herein include mixtures of polysaccharides, hydrophobically modified starches and gelatin or whey protein isolates. The matrix polymer may comprise at least about 40 wt % whey protein isolate, at least about 20 wt % hydrophobically modified starch, and at least about 10 wt % polysaccharides. A preferred matrix polymer mixture comprises about 40-60 wt % whey protein isolate, about 20-40 wt % hydrophobically modified starch, and about 10-30 wt % polysaccharides.

All of the polymers used in the composition may be food-grade biopolymers. As used herein, "food-grade" is defined as any material that is deemed by the United States Food and Drug Administration to be safe for use in food and animal feed products.

According to another aspect of the present invention, a preparation method comprising comprises steps (a)-(d) is provided. In step (a), the pH of a suspension, which comprises a hydrophobic compound and a protein, is reduced to below the isoelectric point (pKa) of the protein. In step (b), the protein in the suspension of step (a) is irreversibly denatured such that hydrophobic compound droplets coated by a shell comprising the irreversibly denatured protein are formed, and the hydrophobic droplets comprise the hydrophobic compound. In step (c), the coated hydrophobic compound droplets of step (b) are mixed with a protein, a starch, and a polysaccharide so that a mixture is formed. In step (d), the mixture of step (c) is dried to form a composition comprising the coated hydrophobic droplets dispersed in a matrix. The matrix comprises the protein, the starch, and the polysaccharide. The composition may comprise less than about 40, 30, 20, 10, 5 or 1 wt % water, preferable less than about 20 wt % water, and more preferably less than about 10 wt % water. The wet mixture of step (c) may be dried by spray drying, freeze drying or any other drying method.

A protein may be irreversibly denatured upon exposure to one or more external stressors. An irreversibly denatured protein is not capable of regaining its native tertiary structure and secondary structure after the removal of the external stressors. Preferably, at least two different types of external stressors are applied sequentially to enhance the hardening of the applied protein coat or shell around the hydrophobic droplets. For example, a mild acid or base or salt treatment is followed by an enzymatic treatment (e.g., transglutaminase), an organic solvent treatment (e.g., alcohol, methanol, acetone, hexane or chloroform), or a heat treatment. A concentrated inorganic salt (e.g., LiBr, NaBr, CaCl2, KSCN, and NaI) may be added so that the pH of the suspension of a hydrophobic compound and a protein is reduced to just below the isoelectric point (pKa) of the protein. This first step may result in the "salting out" and agglomeration of the protein molecules around the hydrophobic compound droplets. This step may be reversed by diluting the suspension or increasing the pH back to above the pKa value of the protein. The salting out or the pH reduction step may then be followed by an enzymatic treatment, brief heating, or adding a cross linking reagent (e.g., Glutaraldehyde, Formaldehyde) to precipitate the protein, forming irreversibly a shell around the hydrophobic droplets. In some preferred embodiments, the pH reduction to just below the pKa value of the protein followed by brief exposure of the suspension to a heat exchanger, for example, for about 1-60 seconds, to raise the temperature to, for example, in the range of about 40-100° C., preferably about 50-90° C., more preferably about 60-85° C.

The shell may comprise one or more irreversibly denatured proteins. The shell may be substantially free of (e.g., having less than about 60, 50, 40, 30, 20, 10, 5, or 1 wt %) proteins that are not irreversibly denatured protein. The shell may comprise at least about 60, 70, 80, 90, 95 or 99 wt % of the irreversibly denatured proteins.

The composition of the present invention may provide pH-controlled release of hydrophobic compounds in neutral to basic conditions of the lower gastrointestinal tract. The composition may reduce or eliminate the unpleasant taste or after-taste and odor of hydrophobic compounds such as fish oil. By encapsulating hydrophobic compounds in the composition of the present invention, possible negative visual and physical changes to consumable products comprising the hydrophobic compounds may be avoided. The resulting consumable products are not only appealing to consumers, but also are stable and have an adequate shelf life. They may also protect sensitive hydrophobic compounds, upon consumption, in the acidic environment of the stomach and allow the release of the hydrophobic compounds to the lower gastrointestinal tract for good absorption and bioavailability.

The coated hydrophobic droplets may be embedded in a polymeric matrix or a mixture of polymeric matrices. The polymeric matrices may comprise water soluble polysaccharides, starches or starch derivatives, and/or proteins. In one embodiment, coated droplets are uniformly dispersed in a mixture of polymeric matrices to form a slurry suitable for spray drying or any known drying method, and the slurry is dried in bulks and milled to form dry and flowable particles. In another embodiment, coated droplets are uniformly dispersed in a paste comprising a polymeric matrix or a mixture of polymeric matrices to form a paste, which is then extruded into a desirable shape or form.

The composition of the present invention may be milled to form dry and flowable particles. In some embodiments, all or at least a majority of the resulting dry particles have a particle size within the range of about 10 μm to about 10 mm, preferably within the range of about 50 μm to about 1000 μm, more preferably within the range of about 100 μm to about 700 μm.

For each preparation method of the present invention, the resulting dry composition is provided.

The dry composition of the present invention may be used in a consumable product. In particular, the dry composition may be included in food, animal feed, nutraceutical and pharmaceutical products.

A consumable product comprising the dry composition of the present invention is also provided. The consumable product may be useful for delivering hydrophobic compounds beneficial to general health and well-being of human or animals, without compromising the product shelf life or any significant extent of the aroma and taste characteristics of the product. The consumable product may have a therapeutic, nutritional, or disease-preventive effect. The product may be selected from the group consisting of food products, nutritional products, ready to drink mixes, supplements in the form of powder, tablet or capsule, vitamin premixes, pelleted animal feed or supplements or premixes, nutraceutical products, pharmaceutical products, and drugs.

A desired amount of a protected and stable hydrophobic compound in the above-described dry compositions may be included in a food or animal feed product. The dry composition may be added to the food animal feed product using conventional techniques known in the art. In some embodiments, the dry composition is sufficiently mixed in the food or animal feed product to provide substantially uniform distribution. For example, a stable vitamin premix in the form of free flowing powder may be compressed into tablets or pellets.

The amount of a hydrophobic compound in a food or animal feed product may vary depending on the desirable application and/or nutritional content. In one embodiment, a food product such as a nutritional bar or a ready-to-drink beverage may include about 5-5000 mg of omega-3 fatty acids per serving size. Other amounts are also contemplated and within the scope of the invention. For example, it may be desirable to provide at least 40 mg of omega-3 fatty acids (combined EPA and DHA) in multivitamin tablets or gumball products to meet the United States Food and Drug Administration (FDA) content claim requirements.

Encapsulation of hydrophobic compounds in the compositions of the present invention or using the methods of the present invention stabilizes and protects the hydrophobic compounds from oxidation and degradation. When included in food or animal feed product, the composition of the present invention may protect the hydrophobic compounds over a suitable shelf-life for the product. The consumable products of the present invention may have a shelf-life greater than one month, e.g., about 1-12 months and possibly up to about 24 months or longer under ambient light and temperature conditions, depending on the type of packaging, and the materials used for packaging the product.

The food or animal feed products may optionally include additional ingredients. The additional ingredients include, for example, vitamins, minerals, sweeteners, flavorings, colorings, thickeners, emulsifiers, acidulants, electrolytes, antifoaming agents, proteins, carbohydrates, preservatives, and mixtures thereof. The additional ingredients can be added at various points during the preparation process, for example, before or after addition of the composition of the present invention. In addition, an inert gas (e.g., nitrogen or argon) headspace may be maintained during the intermediary processing of the product and final packaging. Additionally/alternatively, an oxygen or UV barrier and/or oxygen scavengers could be used in the final packaging.

The hydrophobic compound in the composition of the present invention may remain substantially protected within the polymeric matrix in the acidic environment of the stomach, where the pH is typically about 1-3. The polymeric matrix may release substantially the hydrophobic compound in a pH-controlled manner in a human or animal lower gastrointestinal tract, e.g. the intestine, thus enhancing bioavailability and overall physiological efficacy of the compound.

The hydrophobic compound in the composition of the present invention is stable. For example, at least about 50, 60, 70, 80, 90, 95 or 99 wt % of the hydrophobic compound remain active after being stored an extended period of time (e.g., for at least about 1 day, 1 week, 1 month, 3 months, 6 months, 1 year, 2 years, or 5 years), or being exposed to an acidic environment (e.g., at pH of about 1-3). The composition may be substantially free of (e.g., comprising less than about 10, 5, 1 or 0.1 wt %) an emulsifier or surfactant.

In the composition of the present invention, most of the hydrophobic droplets are coated by a shell comprising one or more irreversibly denatured proteins. For example, at least about 50%, 60%, 70%, 80%, 90%, 95% or 99% of the hydrophobic droplets are coated. The coated hydrophobic droplets are stable. For example, at least about 50%, 60%, 70%, 80%, 90%, 95% or 99% of the coated hydrophobic droplets remain coated after being stored an extended period of time (e.g., for at least about 1 day, 1 week, 1 month, 3 months, 6 months, 1 year, 2 years, or 5 years), or being exposed to an acidic environment (e.g., at pH of about 1-3).

Hydrophobic droplets may be dispersed uniformly in water to form a suspension. The core droplet may include one or more hydrophobic compounds, for example, a liquid such as fish oil or carotenoids. The suspension may comprise one or more hydrophobic compounds at a concentration in the range of about 1-30% (e.g., about 5%, 10%, or 20%) by volume. Antioxidants may be added to enhance the stability of the hydrophobic compound.

The term "about" as used herein when referring to a measurable value such as an amount, a percentage, and the like, is meant to encompass variations of ±20% or ±10%, preferably ±5%, more preferably ±1% from the special value, as such variations are appropriate to perform the disclosed methods.

The following examples are provided to describe exemplary aspects of the invention in greater detail. They are intended to illustrate, not to limit, the invention.

Example 1

Figure 1:
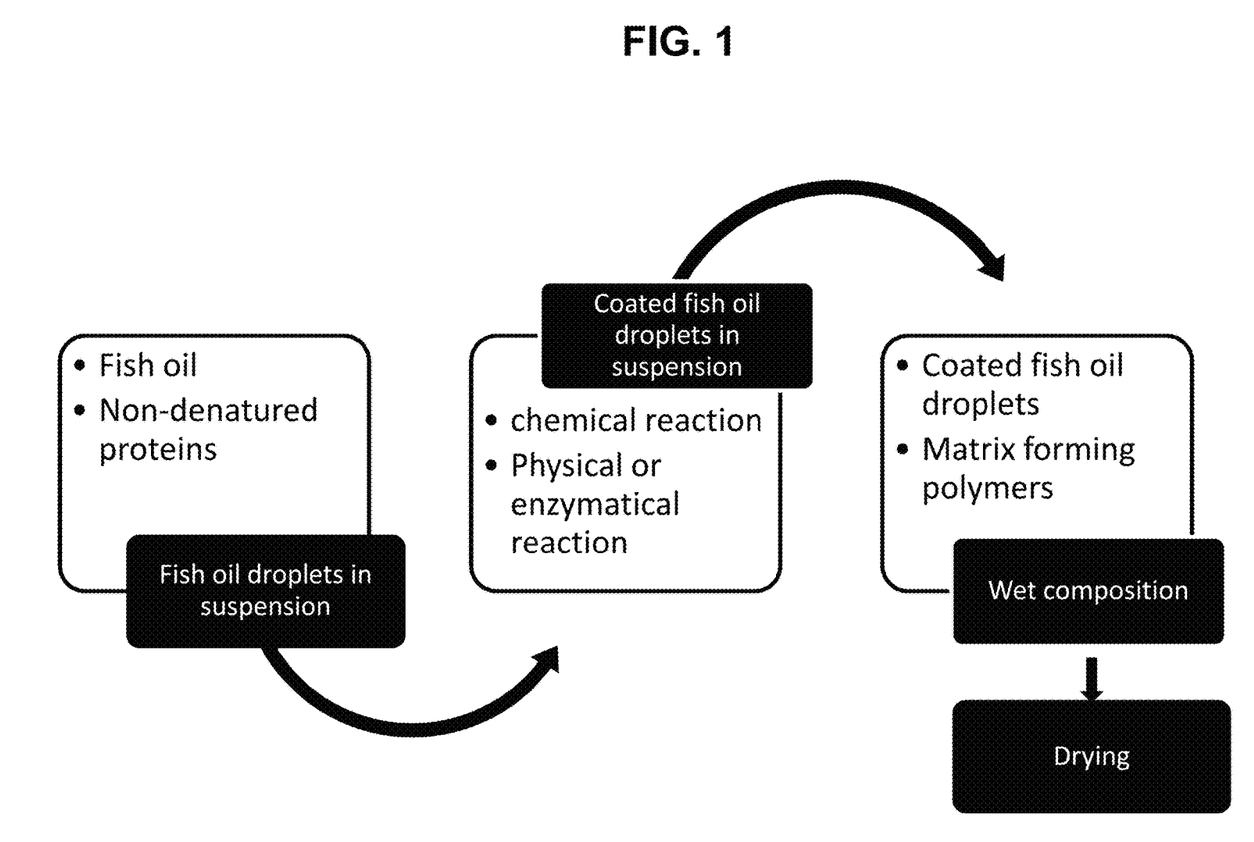

A dry composition containing vitamin A acetate was prepared following the method described in FIG. 1. A 100 mL aqueous solution of 3% by weight of beta lactoglobulin (Davisco, Eden Prairie, Minn.) was prepared. Pure crystalline vitamin A acetate (10 g, Sigma) was added to the 100 mL beta lactoglobulin solution. The mixture was sonicated for twenty minutes in 65° C. water bath to form an oil-in-water suspension. Then, the pH of the suspension was slowly lowered while steering at 400 RPM to between 4.5 and 5.0. Then the mixture was passed through a heat exchanger submerged in boiling water at a flow rate of about 50 ml/min using a peristaltic pump to form a suspension containing vitamin A acetate droplets coated with irreversible denatured proteins. The suspension was immediately cooled in an ice bath under a blanket of nitrogen gas. The particle size of the coated vitamin droplets was about 2.0 to about 7.0 μm. Once the temperature reached 5-10° C., the pH was neutralized using a concentrated 1 M sodium hydroxide. Polymeric matrix was formed with the addition of 50 ml aqueous solution containing 5% w/w whey protein isolate (Bipro, Davisco, Eden Priarie, Minn.), 2% w/w gum acacia and 2% w/w modified food starch (HI-CAP® 100, Ingredien, Westchester, Ill.). The final slurry was spray dried (Lab Spray Dryer-YC-015, SPM., Shanghai Pharmaceutical Machinery CO., Shanghai, China) to form a dry composition containing stable vitamin A acetate according to the present invention.

It should be noted that the sonication in Example 1 could be replaced by or supplemented with high-speed homogenization or the suspension could be microfluidized directly to form a suspension containing sub-micron size of fish oil droplets.

Example 2

A dry composition containing omega-3 fatty acid rich fish oil (400 g, DHA 70TG, purchased through Icelandic Direct, New York, N.Y.) was prepared following the method described in the flow chart of FIG. 1. A 4000 mL aqueous solution of 5% by weight of beta lactoglobulin (Davisco, Eden Prairie, Minn.) was prepared. The fish oil was first added to a 5% w/w antioxidant mixture containing 0.5% resveratrol, 1% Vitamin C palmitate, 1% alfa tocoferoles, 1% rosemary extract and 1.5% soy lecithin, and the stabilized fish oil was then added to the 3000 mL beta lactoglobulin solution. The mixture was mixed in a mixer and then passed through a microfluidizer at 4500 psi (LM-10, Microfluidics, Westwood, Mass.) to form an oil-in-water suspension. The pH of the suspension was slowly lowered while steering at 200-400 RPM to between 4.5 and 5.0. Then the mixture was passed through a heat exchanger submerged in boiling water at a flow rate of about 50 ml/min using a peristaltic pump, to form a suspension containing fish oil droplets coated with irreversible denatured proteins. The suspension was immediately cooled in an ice bath under a blanket of nitrogen gas. The particle size of the coated fish oil droplets was about 0.2 to about 0.7 μm. Once the temperature reached 5-10° C., 1000 ml of 3% w/w chitosan solution was added to the suspension and the pH was neutralized using a concentrated 1 M sodium hydroxide to form a polysaccharide matrix. An additional Polymeric matrix was formed with the addition of 2000 ml aqueous solution containing 5% w/w whey protein isolate (Bipro, Davisco, Eden Priarie, Minn.), and 4% w/w modified food starch (HI-CAP® 100, Ingredion, Westchester, Ill.). The final slurry was spray dried (Niro Mobile Minor GEA, Columbia, Md.) to form a dry composition containing stable fish oil according to the present invention.

The effect of the encapsulation process on the oxidation of the fish oil was determined by Anisidine value analysis following the recommended method of anisidine analysis by the IAFMM (Int. Assc. Fish Meal Manufacturers, London, GB). The results showed that the Anisidine value of the free fish oil as obtained from the manufacturer was 7.15 and the Anisidine value of the encapsulated fish oil according the method of the present invention was 8.3. Thus, the process as described above including the spray drying step did not harmed the fish oil.

Example 3

Figure 2:
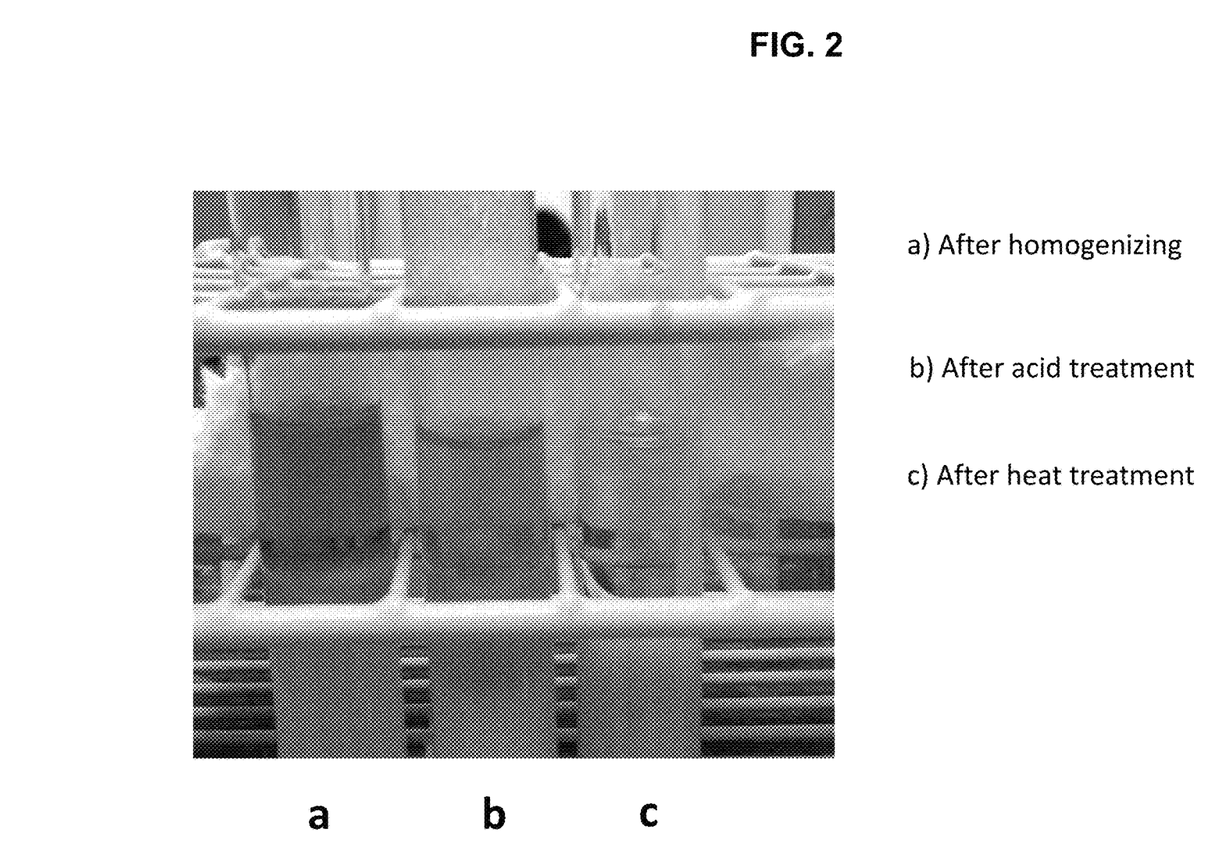
FIG. 2 shows the relative amount of non-coated oil droplets after homogenizing an oil in a non-denatured protein solution (a), after sonication of the homogenized mixture (b), and after heating the sonicated mixture. The fish oil was added with an oil soluble dye and the non-coated oil was extracted with hexane. This figure shows that both steps of acid reduction and heating are essential to minimize the level of the free surface oil or the amount of uncoated oil droplets in the suspension.
Figure 3:
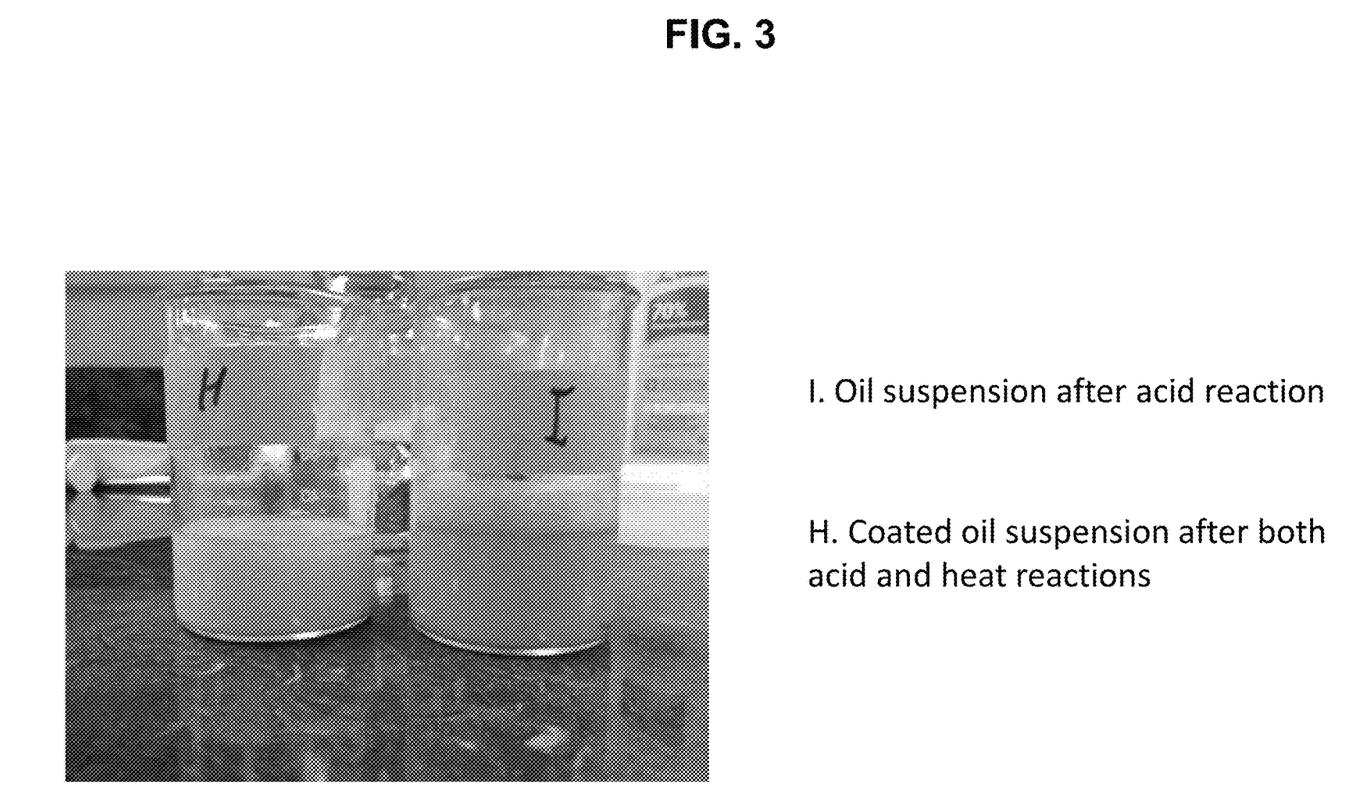
FIG. 3 shows the stability of suspensions containing fish oil droplets coated with denaturable proteins after an acid reaction step and after both acid and heat reaction steps.

To determine which steps in the process described in FIG. 1 are essential, the encapsulated fish oil was pigmented with an oil soluble dye and the free non-coated oil was extracted with hexane from the sample at the end of each step of the process. FIG. 2 shows the relative amount of the non-coated oil after homogenizing the oil in non-denatured protein solution (a), after sonication of the homogenized mixture (b) and after heating the sonicated mixture. FIG. 3 shows the stability of suspensions containing coated oil droplets, with or without the heating step.

Accordingly, it is preferable to micronize fish oil before the formation of the coat or shell with irrepressibly denatured proteins in two sequential steps of chemical and physical reactions.

Example 4

To further determine the essential steps in the process described in FIG. 1, the irreversibly denatured fish oil droplets were spray dried without the addition of matrix forming polymers (by using maltodextrin as a filler) and after the addition of matrix forming polymers. The surface oil was extracted from the dry powders by hexane followed by evaporation of the hexane and gravimetrical determination of the amount of the extracted oil. Table 1 shows the results from the free oil surface analysis of spray-dried compositions with or without matrix forming polymers. Significant reduction in the surface oil was achieved when the matrix forming polymers were added before spray drying the wet composition.

TABLE 1

Free oil surface analysis (% of the total oil in the powder) of spray-dried composition with or without matrix forming polymers

|  | Free oil content (% of total oil) |
| --- | --- |
| Dry composition without matrix forming polymers | 10% |
| Dry composition with matrix forming polymers | 5.7% |

Accordingly, it is preferable to further embed the coated fish oil droplets within a matrix of the polymeric compounds as disclosed in the present invention.

Example 5

Figure 4:
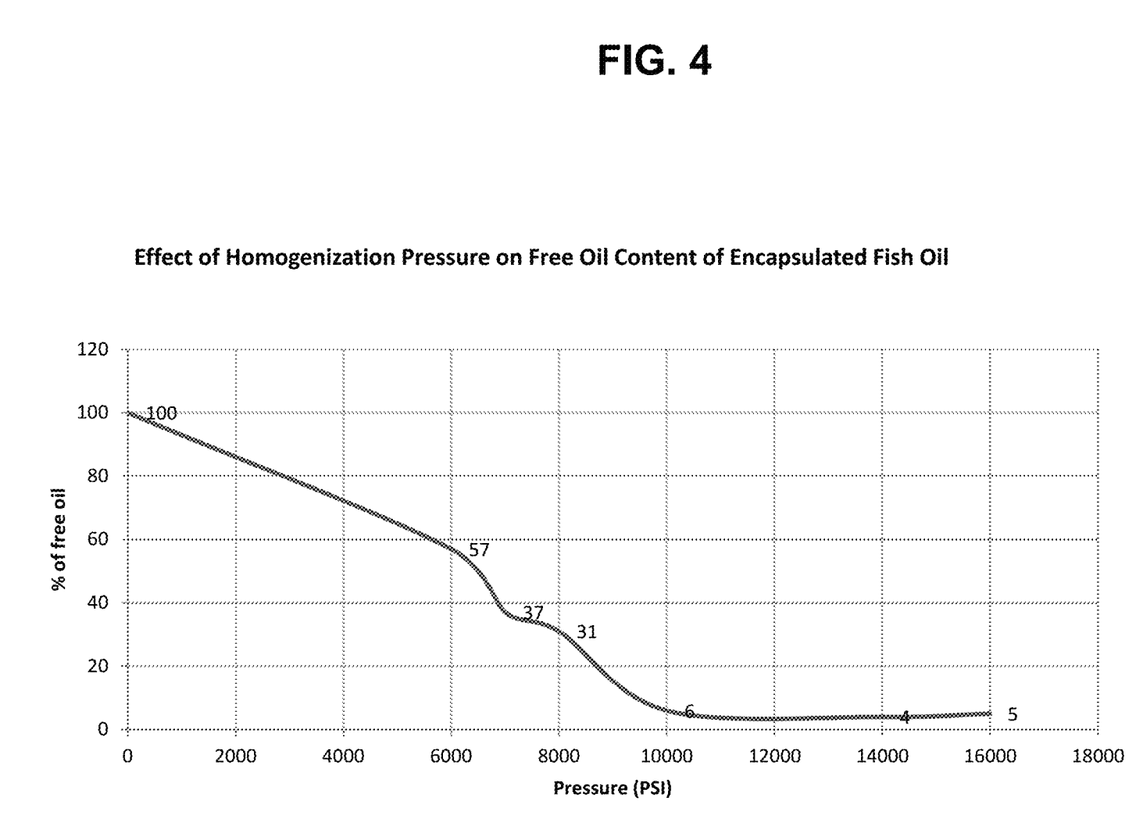
FIG. 4 shows the effect of homogenization pressure on free oil content of encapsulated fish oil.

The optimal homogenization pressure required for the microfluidizing process was established. Dry compositions containing fish oil were prepared as described in Example 2 except that the homogenizing pressure varied between 6000 and 16000 psi. The resulted dry compositions were subjected to free oil surface analysis. The surface oil was extracted from the dry powders by hexane followed by evaporation of the hexane and gravimetrical determination the amount of the extracted oil. FIG. 4 show the effect of the homogenizing pressure on the oil free surface of the resulted particles. It was determined that a homogenization pressure higher than 10K reduces the free oil in the spray dried powder to below 6%.

Example 6

The effect of various antioxidants blends on encapsulation efficiency was evaluated. Dry compositions containing fish oil were prepared as described in Example 2 except that the 5% w/w antioxidant mixture was replaced with various mixtures as described in Table 2. The resulted dry compositions were subjected to free oil surface analysis. The surface oil was extracted from the dry powders by hexane followed by evaporation of the hexane and gravimetrical determination the amount of the extracted oil. The free oil surface analysis results for these various antioxidant oil blends are summarized in Table 2.

TABLE 2

Free oil surface analysis of antioxidant oil blends

| Oil Blends | Free oil content (% of total oil) | Remarks |
|---|---|---|
| Fish oil only | 4-6 | |
| Oil + lecithin + resverotrol + vit E + herblox | 50-60 | Herblox: rosemary oil extract (Kalsec ®, Inc. Kalamazoo, MI) |
| Oil + resverotrol + vit E + Duralox + lecithin | 40-50 | Duralox: rosemary oil extract with vit c acetate (Kalsec ®, Inc. Kalamazoo, MI) |
| Oil + resverotrol + vit E + Duralox + MCT | 15-20 | MCT: medium chain triglycerides |
| Oil + resverotrol + vit E + Duralox + mono-glycerides | 30-35 | |
| Oil + resverotrol + vit E + Duralox | 15-20 | |
| Oil + TBHQ | 25-27 | |
| Oil + Vit E + Herblox + lecithin | 18-22 | |
| Oil + Vit E + Herblox | 5-6 | |
| Oil + Vit E + Herblox + Anise oil | 6-8 | |

The free oil surface analysis results suggest that antioxidants interfered with the encapsulation process, and caused high free oil content on the particle surface. The lowest surface free oil content was obtained with an antioxidant blend containing vitamin E and a rosemary extract. The addition of Anise oil extract to the blend may contribute to better masking of the fishy smell.

Example 7

Oxidized free fish oil and encapsulated fish oil samples were evaluated by an assembly of non-professional panel. The fish oil samples (about 2-4 g) were spread on a petri dish and subjected to oxidation for 12 hours in an incubator at 45° C.; and 100% relative humidity. Table 3 shows a summary evaluation of the sensory panel test. It shows that the encapsulated fish oil in the composition of the present invention was not deteriorated by the forced oxidation treatment.

TABLE 3

Consensus evaluation of a test panel of forced oxidized (12 hours at 45° C. and 100% relative humidity) of encapsulated vs. non-encapsulated fish oil.

| | Consensus evaluation of the sensory panel |
|---|---|
| Free fish oil | Strong fishy odor |
| Free fish oil coated on ingredients of the composition | Mild fishy odor |
| Encapsulated fish oil in the composition of the current invention | Neutral, no fishy odor |

The present invention is not limited to the embodiments described and exemplified above, but is capable of variation and modification within the scope and range of equivalents of the appended claims.

What is claimed is:

1. A composition comprising a hydrophobic compound in a form of coated hydrophobic droplets, wherein more than 90% of the hydrophobic droplets are coated by a shell, wherein the shell comprises an irreversibly denatured first protein, wherein the shell is covered by a polysaccharide matrix, wherein the polysaccharide matrix is covered by a polymeric matrix, and wherein the polymeric matrix comprises a starch and a second protein, and wherein the composition comprises less than 20 wt % water.

2. The composition of claim 1, wherein the hydrophobic compound is a bioactive agent selected from the group consisting of vitamins, antibiotics, carotenoids, plant extracts, fruit extracts, vegetable extracts, antioxidants, lipids, steroids, phytochemicals and drugs.

3. The composition of claim 1, wherein the irreversibly denatured first protein is prepared by applying two different external stressors, wherein each external stressor is selected from the group consisting of an acid, a base, an inorganic salt, an enzyme, an organic solvent, heat and sheer force, and a combination thereof.

4. The composition of claim 1, wherein the hydrophobic droplets have a particle size within the range of 0.1 µm to 5.0 µm.

5. The composition of claim 1, wherein the ratio between the irreversibly denatured first protein and the hydrophobic droplets is within the range of 0.1:1 to 1:1 by weight.

6. The composition of claim 1, wherein the second protein is a globular or randomly coiled protein.

7. The composition of claim 6, wherein the globular or randomly coiled protein is selected from the group consisting of dairy proteins, gelatin, corn zein proteins, bovine serum albumin, egg albumin, proteins from wheat, barley, rye or oats, vegetable proteins, microbial proteins, legume proteins, proteins from tree nuts, and proteins from ground nuts.

8. The composition of claim 1, wherein the polysaccharide is selected from the group consisting of pectin, alginic acid and salts thereof, xanthan gum, chitosan, dextran, pullulan, chondroitin sulfate, gum arabic, gum karaya, gum tragacanth, and carrageenan.

9. The composition of claim 1, wherein the starch is hydrophobically modified.

10. The composition of claim 1, wherein the polymeric matrix further comprises a polymer selected from the group consisting of ethyl cellulose and HPMC.

11. The composition of claim 1, further comprising an antioxidant selected from the group consisting of phospholipids, alpha-lipoic acid, citric acid, Vitamin C and esters thereof, green tea polyphenols, green tea extracts, grape seed extracts, resveratrol, quercetin, cinamic acid and salts thereof, ferulic acid and salts thereof, rosemarinic acid and salts thereof, carotenoids, curcuminoids, superoxide dismutase, glutathione peroxidase, tocoferoles, tocotrienols, polyphenols, Coenzyme Q10, cysteine, methionine, and a combination thereof.

12. The composition of claim 1, wherein the hydrophobic droplets further comprise an edible oil selected from the group consisting of vegetable oils, animal oils, marine oils, and microalgae oils.

13. The composition of claim 12, wherein the vegetable oil is selected from the group consisting of rice bran oil, flaxseed oil, and oil comprising an omega-3 fatty acid or a conjugated linoleic acid.

14. The composition of claim 12, wherein the animal oil is selected from the group consisting of marine oil, fish oil, and egg oil.

15. The composition of claim 12, wherein the microalgae oil comprises an omega-3 fatty acid, an omega-6 fatty acid, or a conjugated linoleic acid.

16. The composition of claim 1, wherein the composition is prepared according to a method comprising
 (a) reducing the pH of a suspension comprising hydrophobic droplets and a first protein to below the isoelectric point (pKa) of the protein, wherein the hydrophobic droplets comprise a hydrophobic compound;

(b) irreversibly denaturing the first protein in the suspension of step (a), whereby the hydrophobic droplets are coated by a shell comprising the irreversibly denatured first protein;

(c) mixing the coated hydrophobic droplets of step (b) with a second protein, a starch, and a polysaccharide to form a mixture; and (d) drying the mixture of step (c), whereby the composition is prepared.

17. A consumable product comprising the composition of claim 1, wherein the consumable product has a therapeutic, nutritional, or disease-preventive effect.

18. The product of claim 17, wherein the product is selected from the group consisting of food products, nutritional products, ready-to-drink mixes, supplements in the form of powder, tablet or capsule, vitamin premixes, pelleted animal feed, supplements or premixes, nutraceutical products, pharmaceutical products, and drugs.

* * * * *